United States Patent [19]

Lenke et al.

[11] 3,997,612
[45] Dec. 14, 1976

[54] POLYTHIAFORMAL COMPOSITIONS

[75] Inventors: Gerd M. Lenke, Dover, Del.; Kent B. McReynolds, Telford, Pa.

[73] Assignee: Reichhold Chemicals, Inc., White Plains, N.Y.

[22] Filed: Dec. 6, 1974

[21] Appl. No.: 530,105

Related U.S. Application Data

[63] Continuation-in-part of Ser. No. 300,685, Oct. 25, 1972, abandoned.

[52] U.S. Cl. .................... 260/609 R; 260/30.8 R; 260/761
[51] Int. Cl.[2] ................................. C07C 149/14
[58] Field of Search ........... 260/609 R, 30.8 R, 761

[56] References Cited

UNITED STATES PATENTS

| 2,668,862 | 2/1954 | Price | 260/609 R |
|---|---|---|---|
| 2,905,720 | 9/1959 | Benneville | 260/609 R |
| 2,905,721 | 9/1959 | Benneville et al. | 260/609 R |
| 3,005,853 | 10/1961 | Wilgus et al. | 260/609 R |
| 3,290,382 | 12/1966 | Hubscher | 260/609 R |
| 3,446,775 | 5/1969 | Bertozzi et al. | 260/609 R |
| 3,503,930 | 3/1970 | Morris et al. | 260/609 R |
| 3,635,736 | 1/1972 | Oftedahl | 260/609 R |

OTHER PUBLICATIONS

Lienhard et al.; J. Am. Chem. Soc. 88 pp. 3982–3995 (1966).
Walker; "Formaldehyde" (1963) pp. 279–280.

*Primary Examiner*—Lewis Gotts
*Assistant Examiner*—D. R. Phillips

[57] ABSTRACT

Water-insoluble compositions are produced by the liquid phase reaction of primary thiadiols with formaldehyde and a monothiol in the presence of a protonic acid catalyst. These compositions have utility as plasticizers.

10 Claims, No Drawings

POLYTHIAFORMAL COMPOSITIONS

CROSS REFERENCE TO RELATED APPLICATIONS

This application is a continuation-in-part of application Ser. No. 300,685 entitled "Novel Plasticizer Compositions and Method for Their Preparation," filed Oct. 25, 1972, now abandoned.

BACKGROUND OF THE INVENTION

This invention relates to new compositions of matter which are useful as plasticizers for polymeric materials. More particularly, this invention relates to a novel class of polymers which are capable of plasticizing a wide variety of both natural and synthetic polymers.

Plasticizers are an important adjunct to the utilization of polymeric materials in that they are widely incorporated in both natural and synthetic polymers to increase the workability, flexibility or distensibility of such materials. In addition, they are often used as extenders for polymeric materials. In the plasticization or extension of polymers, organic plasticizers are generally used which are usually moderately high molecular weight liquids or, occasionally, low-melting solids.

Though there is considerable debate as to the mechanism by which various plasticizers function, most plasticizers for polymeric materials are of the solvent type, i.e. rather high boiling, normally liquid organic compounds which are chemically inert toward the polymers in which they are used, but in which the polymer swells or is at least partially soluble and will therefore be readily softened by intimate contact with the plasticizer. The most widely used solvent-type plasticizers include esters of carboxylic acids or phosphoric acid, hydrocarbons, halogenated hydrocarbons, ethers, glycols and sulfonamides.

In the selection of a plasticizer, it is of particular importance that the plasticizer exercise the effect for which it is intended without undue adverse effect on other properties of the polymeric material and that it be at least comparable in cost and preferably lower in cost than the polymer to which it is added.

A particular problem in the field of plasticization has been the plasticization of polymeric materials which are to be exposed to high temperatures under oxidative conditions. Plasticizers for this application must be non-volatile, must be compatible with the base polymer and must maintain the flexibility of the polymer, all of which must be done without significant impairment of the other performance properties of the polymeric material.

A new class of water-insoluble compositions which have utility as plasticizers has been discovered which not only has the above-described capabilities to plasticize high temperature performance polymers, but also to improve the resistance of such polymers of oxidative deterioration.

DISCUSSION OF THE PRIOR ART

In U.S. Pat. No. 2,785,947, Kress and Abrams disclose the use of polyacetals of monoaldehydes and dialdehydes containing up to 8 carbon atoms to treat fabrics and thus improve their laundry and dry cleaning durability. The disclosed polyacetals are water-soluble. Kress, in U.S. Pat. No. 2,785,949, discloses the use of polyacetals like those disclosed in U.S. Pat. No. 2,785,947 as substitutes for melamine resins to give dimensional stability to cellulosic textile materials. In U.S. Pat. No. 2,785,995 to Kress, the same type of polymeric acetals are used to improve the wet strength of paper. Matuszak et al in U.S. Pat. No. 2,796,401 disclose the use of complex formals prepared by reacting formaldehyde, mono-alcohols and polyhydric alcohols as a lubricant base. The polyformals disclosed are water-soluble. In U.S. Pat. No. 2,786,081 to Kress, the inventor discloses the use of water-soluble aldehyde/polyol condensation products as plasticizers "either of water-soluble or organic-soluble polymers." However, no example of such use is given. Cottle and Young, in U.S. Pat. No. 2,796,423, reveal the use of polyformals similar to those of U.S. Pat. No. 2,796,401 as synthetic lubricants. Mertzweiller, in U.S. Pat. No. 2,796,441, discloses the use of polyformals of formaldehyde and long chain mono-alcohols derived from the Oxo process as synthetic lubricants. In U.S. Pat. No. 2,838,573, Matuszak and Ready disclose the preparation of complex formal lubricants by reacting formals with a glycol. Johnson in U.S. Pat. No. 2,846,404 discloses the use of polyformals to inhibit foam in steam boilers. Kress, again, in U.S. Pat. No. 2,878,294, discloses water-soluble polyacetals prepared by reacting polyalkylene glycol or thiodiglycol, monohydric alcohol and aldehydes, which products are said to be useful as hydraulic fluids. However, no examples are set forth in Kress that show the reaction of the thiodiglycol.

The above-described polyformals of the prior art would not, however, be useful as plasticizers for polymers such as nitrile and chloroprene rubbers because they are substantially incompatible therewith. Moreover, they would not enhance the heat and oxidation resistance of the polymer to which they were added since they contain no component or functional group capable of taking part in an anti-oxidative chemical reaction.

Thus, while the prior art teaches much about the composition and properties of water-soluble polyformals and various uses therefor, there is no suggestion of the unique properties and uses of the water-insoluble composition of the present invention.

DESCRIPTION OF THE INVENTION:

The composition of the present invention may be broadly characterized structurally as a polythiaformal and is represented by the following chemical structure:

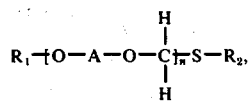

wherein $R_1$ is selected from the group consisting of hydrogen and the monovalent group

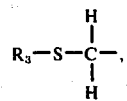

$R_2$ is a hydrocarbyl group having from 1 to 30 carbon atoms, $R_3$ is independently selected from the group consisting of hydrocarbyls having from 1 to 30 carbon atoms, A is the divalent residue of a thiadiol, and $n$ is an integer from 1 to 40, inclusive.

Compounds of the above general formula may be prepared by the liquid phase reaction of thiadiol, formaldehyde and a hydrocarbyl thiol (mercaptan) in the presence of a protonic acid catalyst. The primary product of the reaction is a polymeric thiaformal in which the ends of the polymer chains are terminated (endcapped) with the hydrocarbyl residue derived from the thiol. Endcapping of this nature is carried out simultaneously with formation of the polythiaformal structure. However, the reaction mixture will ordinarily be expected to contain minor amounts of non-endcapped polymers.

Protonic acid denotes acids which, in an appropriate solvent having a high dielectric constant, such as water, are capable of dissociation into a proton and an anion and which have a Dissociation Constant of at least $1 \times 10^{-5}$ and preferably of at least $1 \times 10^{-2}$ (measured in water).

It is preferred to employ primary thiadiols in synthesizing the compositions of the invention, because of the tendency of the corresponding secondary alcohols to undergo undesirable side reactions.

The following are examples of primary thiadiols which may be used to make the polythiaformal compositions of the present invention:

3-thiapentane diol - (thiodiglycol)

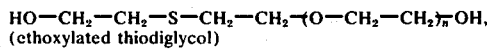
(ethoxylated thiodiglycol)   $n = 1-5$

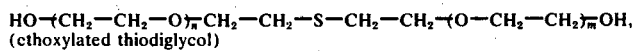
(ethoxylated thiodiglycol)   m or $n = 1-5$

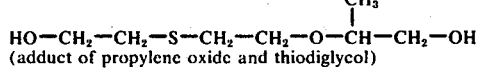
(adduct of propylene oxide and thiodiglycol)

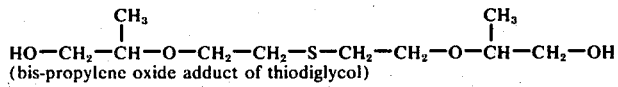
(bis-propylene oxide adduct of thiodiglycol)

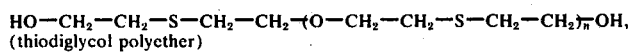
(thiodiglycol polyether)   $n = 1-5$

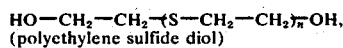
(polyethylene sulfide diol)   $n = 2-6$

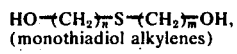
(monothiadiol alkylenes)   $n = 2-4, m = 3-10$

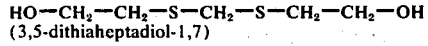
(3,5-dithiaheptadiol-1,7)

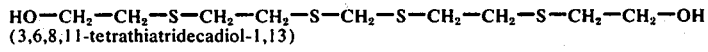
(3,6,8,11-tetrathiatridecadiol-1,13)

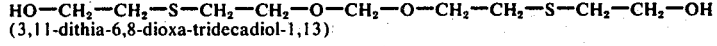
(3,11-dithia-6,8-dioxa-tridecadiol-1,13)

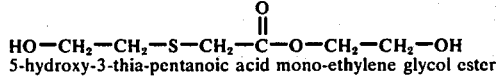
5-hydroxy-3-thia-pentanoic acid mono-ethylene glycol ester

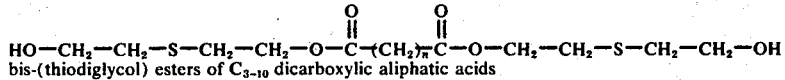
bis-(thiodiglycol) esters of $C_{3-10}$ dicarboxylic aliphatic acids   $n = 1-8$

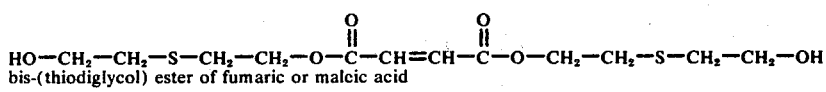
bis-(thiodiglycol) ester of fumaric or maleic acid

DEFINITIONS:

Within the context of the invention, various terms used herein have the following special meanings:

Thiadiol refers to thia-dihydric alcohols of the configuration HO-R-S-R-OH, in which S denotes sulfur. It should be noted that such linkages are sometimes referred to in the art as thioether linkages.

Hydrocarbyl refers to the following hydrocarbon radicals:
  alkyls
  alkenyls
  alkynyls
  aryls
  arylalkyls (aralkyls)
  alkylaryls (alkaryls)

Preferred primary thiadiols are those having from 2 to 20 carbon atoms, especially thiadiols containing 3 to 10 carbon atoms.

Formaldehyde rapidly reacts with the mercapto groups of the monothiol or the hydroxy groups of the thiadiol to form non-volatile hemiformal compounds which then condense further to formal linked polymers. Water is produced in this reaction which could bind any free unconverted aldehyde to a non-volatile hydrate. It is preferred to use paraformaldehyde as a source of formaldehyde since it is relatively non-volatile and depolymerizes readily under reaction conditions. The free aldehyde is almost instantly used up in the formation of hemiformal.

Preferred monothiols which may be used to produce the hydrocarbyl terminated polythiaformals of the invention have the general configuration R—SH in which R is a hydrocarbyl group containing from 4 to 30 carbon atoms. Most preferred are primary mercaptans with alkyl or aralkyl groups containing 8 to 20 carbon atoms. Alkyl esters of thioglycolic acid may be used as well. Exemplary of monothiols which may be used are the following:

n-butyl mercaptan
iso-butyl mercaptan
n-octyl mercaptan
2-ethyl-hexyl mercaptan
n-dodecyl mercaptan
mixed $C_{12-13}$ primary mercaptans
hexadecyl mercaptan
iso-octyl thioglycolate
cyclohexyl mercaptan
mixed primary tridecyl mercaptans*
n-nonyl mercaptan
benzyl mercaptan
p-chlorobenzyl mercaptan
dodecyl benzyl mercaptan
dodecyl thioglycolate
tridecyl-3-mercapto propionate
*Pennwalt Corp.

From the foregoing discussion of the monothiols and thiadiols which may be used, it will be apparent that the reactivity of the thiol and hydroxy groups thereof is an important criterion for synthesis of the compositions of the invention.

By selecting monothiols and diols as to size (molecular weight), configuration and polarity, the products of the invention can be varied widely in compatibility, efficiency, permanence and solvent power for particular polymers. Thus, the selection of particular monothiols and thiadiols may be used as a means of "tailoring" the molecule for use in a particular polymer matrix.

The above-referred thiol and thiadiol residues may be of either acyclic or cyclic configuration as well as combinations thereof and include hetero atoms such as sulfur, nitrogen and oxygen and substituent groups such as halogen, and carboxyl groups. The monothiol residues and the thiadiol residues, therefore, include both substituted and unsubstituted thia-alkyl, and oxa-alkyl groups. Amine substituents are to be avoided.

Protonic acids which may be used to catalyze the reaction of the thiadiol with formaldehyde broadly include alkaryl sulfonic acids and specifically include sulfuric acid, hydrochloric acid, hydrobromic acid, chlorosulfonic acid, phosphoric acid, p-toluene-sulfonic acid, dodecyl benzene sulfonic acid and other strong organic acids, such as trichloroacetic and trifluoroacetic acids. Lewis acids, such as, $AlCl_3$, $BF_3$ and $BF_3$ etherate may also be used to catalyze the reaction, since they are rendered protonic in the presence of the alcohol reactants or even small amounts of water in the reaction system, which would result from the condensation reactions or might be present as an impurity in the starting materials. Sulfuric acid and strong organic acids, such as p-toluene sulfonic acid, dodecylbenzene sulfonic acid and trifluoroacetic acid, are preferred catalysts.

DESCRIPTION OF THE PROCESS

One advantage of the unique plasticizer compositions of the invention is that they are quite easy to synthesize and require only basic production equipment and moderate conditions of reaction pressure and temperature.

Basically the method of synthesis is a single-step process in which all of the reaction components and the catalyst are charged simultaneously.

The process may be carried out as a bulk liquid phase reaction in which at least one of the reactants is a liquid and is capable of acting as a dispersing medium for the other reactants. Thus, while any of the reactants may be normally solids, they nevertheless must be dispersible in the liquid reactant medium and be reactive when so dispersed. Consequently, the reactants useful in the practice of the invention must be dispersible in the reaction mixture in at least one of the following ways: (1) solubility in at least one other reactant which is liquid; (2) non-solution dispersibility in at least one other reactant which is liquid; (3) solvency for at least one other reactant; and (4) constitution as a liquid phase in which at least one insoluble reactant is dispersible.

In most instances, the thiadiol is liquid at reaction conditions and the other reactants — whether liquids or solids — are soluble therein. One notable exception is paraformaldehyde which is insoluble in the reaction system, but upon dispersion therein is depolymerized by the presence of the catalyst to formaldehyde gas, which almost instantly takes part in the formation of a hemiformal, as discussed hereinabove.

The process must be carried out at elevated temperatures and therefore requires heating to about 120° C to obtain adequate reaction rates. However, temperatures of at least about 140° C are preferred to speed the reaction and also to facilitate separation of water formed during the reaction. Since water is formed by reaction of the formaldehyde with the thiadiol to form formal linkages, it is advantageous to remove the water by stripping in order to shift the equilibrium of the reaction to favor formal formation. One molecule of water is formed for each formal bond. So far as is known, the maximum reaction temperature is limited only by the volatility and/or thermal stability of the reactants and products therefrom.

The synthesis of this new class of compounds is not sensitive to pressure variations and may be conducted at atmospheric pressures. Vacuum conditions may be useful in the latter stages of the reaction to remove water and other volatiles from the system.

The process can be carried out under air or an inert atmosphere, such as nitrogen or inert gas (essentially $N_2$ and $CO_2$). Inert atmospheric blanketing is ordinarily preferred because of safety considerations.

The end product of the reaction is comprised of a complex mixture of polythiaformals. When the mercaptan endcapping is less than complete, the reaction product contains a mixture of totally endcapped molecules and minor amounts of mono-endcapped molecules. Normally, the reaction of the mercaptans is rapid and quantitative and the stripped product is homogeneous. If a stoichiometric amount of mercaptan is used, the reaction of the mercaptan is so utterly complete that no trace of mercaptan odor remains in the mercaptan-terminated product.

Water absorbing materials may also be used to remove reaction water from the product, e.g. $CaCl_2$, $CaSO_4$, $Al_2(SO_4)_3$, $Na_2SO_4$, $MgCl_2$, $MgSO_4$, NaCl, KCl, silica gel, molecular sieves and the like. In addition, hydrocarbon solvents may be admixed with the reaction mixture to form azeotropic mixtures with the reaction water, by which removal of the water by distillation can be facilitated. Although, generally, the use of such stripping agents is not preferred, examples of such solvents are benzene, toluene and zylene. These azeotroping agents may also serve as diluents.

In some instances, it may be preferred to neutralize and/or remove the acidic catalyst residues upon completion of the reaction. This may be readily accomplished by means of the addition of an acid acceptor or preferably, a base. Suitable bases include NaOH, KOH, $Na_2CO_3$, $NaHCO_3$ and $K_2CO_3$ in powder, flake or pelletized form. Acid acceptors include molecular sieves, ion exchange resins, silicate polymers, aluminum oxides and the like.

Though the process is basically a single step process, it may be conducted by incremental or continuous addition of one or more of the reactants. It may be conducted as either a batch-wise or continuous operation.

Although it is contemplated that the compositions of the invention will have the greatest utility for the plasticization of nitrile and polychloroprene rubbers, it will, of course, be realized that they may be effective for plasticizing and/or extending other polymeric materials such as SBR, polybutadiene, polyvinyl acetate, polyvinyl chloride, polyvinylidene chloride, polystyrene, natural rubber and many other natural and synthetic polymers. It appears that the plasticizers of this invention are less suited for the plasticization of most substantially saturated all-hydrocarbon polymers, such as poly-$\alpha$-olefins, e.g. polyethylene, polypropylene, poly-n-butene, polyisobutene and copolymers thereof, including such elastomers known as EPM and EPDM.

Preferred is the use of the present composition in polymers of organic monomers which also contain atoms other than hydrogen and carbon. Exemplary of such monomers are carboxylic acids (acrylic, methacrylic, fumaric, maleic and itaconic acids), acrylic and methacrylic acid derivatives (acrylonitrile, methacrylonitrile, acrylamide, methacrylamide, N-methylolacrylamide), vinyl esters (vinyl acetate), vinyl ethers, vinyl ketones, and vinyl heterocyclic compounds (N-vinyl pyrrolidone and vinyl pyridines).

In the case of copolymers of $\gamma$-olefins with other copolymerizable monomers which are $\alpha$-olefins, the compositions of the invention are more effective plasticizers when the $\alpha$-olefin content of such polymers is below about 80 mole percent and preferably below about 70 mole percent.

In the formulation of polymers utilizing the composition as plasticizers, the amount of plasticizer relative to the polymer can be varied over a wide range, depending, of course, upon (1) the character of the particular plasticizer; (2) the character of the polymer; (3) the type of modification which is sought for the polymer; and (4) the extent of polymer modification which is sought.

When the plasticizers of the present invention are employed in neoprene rubbers, i.e. polychloroprenes and in nitrile rubbers, such as copolymers of butadiene and acrylonitrile, it is a particular preferred embodiment that there also be present an activator. The presence of the activator in combination with the plasticizers imparts to such rubbers improved heat and oxidation resistance. Of course, the degree to which such properties are imparted to the rubbers depends on the particular formulation and on the compounding thereof.

In the case of neoprene rubbers, the hydroxy content of the plasticizers should be below about 1 meq. OH/g (determined by the acetic anhydride method of C. L. Ogg and W. L. Porter, Ind. Eng. Chem. Anal; Ed. 17, pp. 394–397 (1945)), and most preferably the hydroxy content should be below about 0.5 meq. OH/g. At higher hydroxy contents, the plasticizers will effect premature curing of the neoprene green stock. The number average molecular weight (Mn) of the plasticizers used in neoprene rubbers should typically be in the range from about 500 to about 2000 and preferably from about 700 to about 1500. The plasticizers may be present in amounts of from about 5 to about 50 and preferably from about 10 to about 30 parts per hundred rubber (phr).

In the case of copolymers of butadiene and acrylonitrile, generally, the greatest improvement in heat and oxidation resistance has been observed when the activator used was zinc oxide, magnesium oxide, cadmium oxide or mixtures thereof. The most preferred activator is cadmium oxide. Typically, the activator will be present in the range of from about 2 to about 30 parts by weight based on 100 parts of the rubber (phr) and preferably in the range of from about 3 to about 15 phr. Moreover, to obtain optimum benefits of the plasticizers; it is important that they have a hydroxy content of at least about 1 meq. OH/g and number average molecular weight (Mn) of at least about 400. The amount of plasticizer used in copolymers of butadiene and acrylonitrile may vary widely depending upon a number of factors, for instance, the particular method used for polymerization and the exact composition of the polymer. Generally, however, the amount present will be in the range of from about 2 to about 40 phr and most preferably in the range of from about 5 to about 20 parts per hundred rubber (phr).

The invention will be better understood by reference to the following examples in which all proportions are expressed in parts by weight unless otherwise indicated.

In expressing the hydroxy content of the present composition, it should be distinctly understood that the analytical method set forth by C. L. Ogg and W. L. Porter (Ind. Eng. Chem. Anal; Ed. 17, pp 394–397 (1945)) was followed, since a number of methods for obtaining hydroxy content are known in the art and the numerical values obtained will vary somewhat depending upon the exact method used.

EXAMPLE I

The synthesis of a mercaptan endcapped product of the invention is illustrated by the following procedure in which the process was carried out in a nitrogen-purged glass reaction vessel equipped with a sealed mechanical stirrer, thermometer, reflux condenser, Dean-Stark trap and inlet and outlet means for the purge gas.

The above-described vessel was first charged with 122 g (1 mole) commercial grade thiodiglycol (TDG), 47 g (1.5 mole) paraformaldehyde and 6 g (1.6% wt.) of dodecyl benzene sulfonic acid catalyst (BioSoft S100 — Stepan Chemical Co.). The reaction vessel was then placed in a heating mantle and heated to about 100° C. After about ½ hour, most of the dispersed paraformaldehyde was dissolved and some water had formed, indicating reaction between the TDG and formaldehyde. After about one hour, when the paraformaldehyde was completely dissolved, a dropping funnel was attached to the reaction flask and 202 g (1 mole) of dodecyl mercaptan (DDM) was added dropwise to the reaction mixture over a period of about 30 minutes. With a Dean-Stark trap placed between the reaction flask and a reflux condenser, the reaction mixture was heated to distill off water which had formed. After 100 minutes, the reaction temperature was 147° C and the theoretical amount of reaction water (28 ml) had been collected in the Dean-Stark trap plus a small organic top layer of about 7 ml. The amount of water obtained indicates complete conversion of the reactants. However, to remove all remaining volatiles, a vacuum (ca. 20 mm Hg) was applied to the system for two hours at 90°–150° C during which 4 ml of additional volatiles were collected in a dry ice-cooled receiving flask. The liquid reaction product was then allowed to cool to room temperature. Yield of water-insoluble reaction product was 291 g. Upon standing overnight the product crystallized to a waxy solid which readily remelted in hot water.

The product was free of mercaptan odor and, though insoluble in water, was easily dispersible (emulsifiable) therein. The product was soluble in acetone, methylethylketone and toluene.

Hydroxyl analysis of the product indicated that it contained 0.12 meq. OH/g. The number average molecular weight (Mn), as determined by vapor phase osmometry, was 590. These data showed that the product contained only about 0.06 OH groups per average molecule and was therefore 97% endcapped with dodecyl mercaptan. Sulfur content was 20.6% wt. The resulting product apparently conforms to the following structure:

| Thiodiglycol | 366 g (3 moles) |
|---|---|
| Paraformaldehyde | 93 g (3.1 moles) |
| Dodecylmercaptan | 202 g (1 mole) |
| Dodecyl benzene sulfonic acid (BioSoft S100 - Stepan Chemical Co.) | 1.5% wt. |

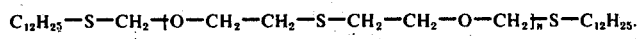

in which $n$ is about 2 or 3 for most molecules of reaction product.

EXAMPLE II

A higher molecular weight mercaptan endcapped product of the invention than described in Example I was prepared by the same procedure as Example I using the following reactant charge:

The reaction product was a water-insoluble liquid but became a waxy solid upon standing at room temperature. The yield was 548 g. The product was free of mercaptan odor. Analytical data of the product were as follows:

| meg. OH/g | 0.11 |
|---|---|
| Mn | 1,000 |
| Sulfur | 23.1% wt. |
| 0.1 OH groups/molecule (95% endcapped) | |

EXAMPLE III

This example illustrates the use of primary tridecyl mercaptan (TDM) as the endcapping agent. The charge was as follows:

| Thiodiglycol | 122 g (1 mole) |
|---|---|
| Paraformaldehyde | 50 g (1.7 mole) |
| Primary tridecylmercaptan | 114 g (0.5 mole) |
| Dodecyl benzene sulfonic acid (BioSoft-S100 - Stepan Chemical Co.) | 5 g (1.6% wt.) |

The general procedure of Example I was followed but in this instance, all the reactants were charged at the start of the reaction and water of reaction was distilled off at 105°–146° C after all the paraformaldehyde was dissolved. Residual volatiles were recovered under vacuum at 90°–140° C.

The clear water-insoluble product was liquid at room temperature and possessed no mercaptan odor. The product yield was 221 g. Analytical data of the product were as follows:

| meq. OH/g | 0.2 |
|---|---|
| Mn | 925 |
| Sulfur | 21% wt. |
| OH groups/molecule | <0.2 |

EXAMPLE IV

The procedure of Example III was repeated except that the tridecylmercaptan was added dropwise after most of the paraformaldehyde had dissolved. The water-insoluble product, a clear amber liquid having no discernible mercaptan odor, was produced at a yield of 220 g. Analytical data of the product were as follows:

| meq. OH/g | 0.18 |
|---|---|
| Mn | 750 |
| OH groups/molecule | 0.14 |

EXAMPLE V

The procedure of Example III was repeated using 3 g p-toluene sulfonic acid catalyst instead of dodecyl benzene sulfonic acid. The water-insoluble product, a clear amber colored liquid having no discernible mercaptan odor, was produced at a yield of 227 g. Analytical data of the product were as follows:

| meq. OH/g | 0.11 |
|---|---|
| Mn | 850 |
| OH groups/molecule | <0.1 |

EXAMPLE VI

This example illustrates the preparation of a tridecyl endcapped product similar to that prepared in Example I but with a higher number average molecular weight using the same procedure as Example V using the following reactant charge:

| Thiodiglycol | 305 g (2.5 moles) |
|---|---|
| Paraformaldehyde | 80 g (2.6 moles) |

-continued

| Primary tridecylmercaptan | 114 g (0.5 mole) |
| p-Toluene sulfonic acid | 5 g (1% wt.) |

400 g of clear liquid amber water-insoluble product were produced. Analytical data of the product were as follows:

| meq. OH/g | 0.23 |
| $\overline{M}n$ | 1180 |
| OH groups/molecule | <0.3 |
| Sulfur, % wt. | 23.3 |

EXAMPLE VII

The procedure of Example VI was repeated except that concentrated sulfuric acid was substituted for p-toluene sulfonic acid as the protonic acid catalyst. The reactant charge was as follows:

| Thiodiglycol | 305 g |
| Paraformaldehyde | 80 g |
| Primary tridecylmercaptan | 114 g |
| $H_2SO_4$, conc. | 1 ml |

415 g of light amber, water-insoluble liquid having 0.27 meq. OH/g was produced.

This example was repeated twice using the identical procedure, except that all the reactants were charged at the same time. The products were light amber in color, were water insoluble and contained 0.17 and 0.21 meq. OH/g, respectively. As with the other plasticizer produced in accordance with the present invention, these products had no mercaptan odor.

EXAMPLE VIII

Three mercaptan-endcapped plasticizing compounds were prepared by the procedure of Example I. The following reactant charges were used:

|  | A | B | C |
|---|---|---|---|
| Thiodiglycol | 122 g | 122 g | 122 g |
| Paraformaldehyde | 50 g | 47 g | 47 g |
| Tridecylmercaptan | 114 g | — | 216 g |
| Dodecyl mercaptan | — | 202 g | — |
| Dodecyl benzene sulfonic acid | 5 g | 6 g | 6 g |
| Analytical Data | A | B | C |
| Yield, % wt. of charge | 76 | 77 | 80 |
| $\overline{M}n$ | 925 | 590 | 620 |
| meq. OH/g | 0.2 | 0.12 | 0.19 |
| Sulfur, % wt. | 21 | 20.6 | —* |

*Sulfur content not determined.

The above-described water-insoluble products were then compounded into a polychloroprene rubber on a conventional two-roll mixing mill in accordance with the following formulation:

| Vulcanization agent (NA-22 - duPont Co.) | 1.0 | |
| Accelerator (dodecylmercaptan) | 1.5 | |
| Activator (10 phr ZnO 4 phr Maglite D-MgO) | 14.0 | parts by weight, basis 100 parts |
| Promoter (Stearic acid) | 0.5 | by wt. dry rubber (phr) |
| Reinforcing agents (20 phr SRF Black 80 phr Dixie Clay) | 100 | |
| Antioxidant (Akroflex DAZ-100 duPont Co.) | 3.0 | |

Each of the above three compounded rubbers was oven cured at 163° C until 100% cure was obtained as measured on a Monsanto Rheograph. Samples of the cured rubbers were then formed into Type C dumbbells and the tensile and elongation properties of each dumbbell determined on one-half of the dumbbell samples. The other half of the dumbbell samples were aged in an air-circulating oven for 70 hours at 135° C at the conclusion of which the cooled samples were measured as to their tensile and elongation properties. The results are set forth in Table I below.

TABLE I

Effect of Oxidative Heat Aging Upon Plasticized Polychloroprene Rubbers

| Plasticizer | A | B | C |
|---|---|---|---|
| $T_b$ - initial[1] | 1894 | 2072 | 1842 |
| $T_b$ - aged[1] | 1602 | 1502 | 1546 |
| T Loss (Gain) | 15.4 | 27.5 | 16.1 |
| $E_b$ - initial[2] | 568 | 602 | 552 |
| $E_b$ - aged[2] | 365 | 330 | 320 |
| % Loss | 35.8 | 45.2 | 42.0 |
| Hardness, Initial[3] | 65 | 66 | 66 |
| Hardness, aged[3] | 74 | 74 | 76 |
| Gain | 9 | 8 | 10 |

[1]$T_b$ denotes tensile strength at break as measured on an Instron tensile tester per ASTM Test Procedure D-412-68.
[2]$E_b$ denotes the % elongation at break as measured on Instron tensile tester per ASTM Test Procedure D-412-68.
[3]Per ASTM Test Procedure D-2240-68.

The above data show that the compositions of the invention are effective plasticizers for rubbers which are subject to oxidative heat aging.

EXAMPLE IX

The products of Examples II and VI were compounded into a typical nitrile rubber (Paracril BJLT from Uniroyal Chemical) and the resulting rubbers were compared with the same nitrile rubber plasticized with a commercial plasticizer (dioctylphthalate) for high temperature properties.

A master batch was prepared as follows:

| Ingredients | Parts |
|---|---|
| Paracril BJLT (Uniroyal Chemical) | 100 |
| Zno | 5 |
| Plastanox 2246 (American Cyanamid) | 2 |
| Spider Sulfur | 1 |
| Hi-Sil EP (Pittsburgh Plate Glass) | 60 |
| Stearic Acid | 0.5 |
| Monex (Uniroyal Chemical) | 0.6 |
| Sunproof junior (Uniroyal Chemical) | 5 |
| $TiO_2$ | 10 |

To three equal portions of this master batch were added separately 20 phr of the two plasticizers from Examples II and VI and dioctylphthalate (DOP) and mixed on a two-roll rubber mill. The three plasticized batches and a portion of the unplasticized master batch (control) were then tested for scorch and minimum cure times at 163° C with the aid of a Monsanto Rheometer. Each rubber composition was cured for 10 minutes at 163° C. A portion of test specimens prepared from each cured composition was used in the tests set forth in Table II.

TABLE II

Effect of Oxidative Heat Aging Upon Plasticized Nitrile Rubber

| Plasticizer Rheometer data | Ex. II | Ex. VI | DOP | None |
|---|---|---|---|---|
| 1 point rise at 163°C (sec) | 195 | 185 | 180 | 142 |
| 100% cure (minutes) | 10 | 10 | 10 | 10 |
| $T_b$-initial[1] | 1571 | 1634 | 1654 | 2242 |
| $T_b$-aged[2] | 1932 | 2043 | 2286 | 2736 |
| $T_b$-aged[3] | 1692 | 1471 | 1153 | 1021 |
| $E_b$-initial[1] | 926 | 910 | 882 | 782 |
| $E_b$-aged[2] | 710 | 665 | 433 | 338 |
| $E_b$-aged[3] | 170 | 123 | 50 | 32 |
| Hardness-initial[1] | 60 | 61 | 64 | 72 |
| Hardness-aged[2] | 66 | 69 | 70 | 79 |
| Hardness-aged[3] | 82 | 80 | 86 | 88 |

[1] See footnote to Table I
[2] Aged in a circulating-air oven for 70 hours at 122° C and tested in accordance with procedure set forth in footnote of Table I.
[3] Aged in a circulating-air oven for 70 hours at 135° C and tested in accordance with procedure set forth in Table I.

The data in Table II show the following:
1. The plasticizers of the invention reduce scorchiness of the unvulcanized stock as compared to the DOP containing product and the control, but minimum cure times are not adversely affected.
2. The plasticizing efficiency of the products of this invention is high, as apparent from the increase of elongation and the decrease in hardness after cure over the unplasticized control and even over the product containing DOP.
3. The most significant advantage of the plasticizers of this invention is demonstrated by their effect on the resistance towards heat aging of the cured vulcanizates. This is evident from the relatively lower changes in elongation and the high final elongations determined after oven aging, as compared to the product containing DOP and the control. This advantage is further evident from the lower hardness and lesser changes in tensile strength of the vulcanizates containing the plasticizers of this invention over both controls, especially in the case of the most severe heat aging.

What is claimed is:

1. A new water-insoluble polymeric composition having polythiaformal linkages therein, of the formula:

$R_1\text{--}[O\text{--}A\text{--}O\text{--}CH_2\text{--}]_n S\text{--}R_2$, wherein $R_1$ is selected from the group consisting of hydrogen and the group $R_3$—O—$CH_2$—; $R_2$ and $R_3$ are independently selected from the group consisting of hydrogen and the monovalent residue of monothiols, said residue of monothiols being present in the statistical average polymer chain at least to about 50 mole percent of the terminal groups; A is the divalent residue of thiadiols having at least 4 carbon atoms; and $n$ is an integer from 2 to 40, said monothiols selected from the group consisting of primary alkyls and aralkyls and mixtures thereof, and said thiadiols selected from the group consisting of primary thiaalkylenes, oxa-thiaalkylenes and mixtures thereof.

2. The composition of claim 1 in which the divalent residues of thiadiols are primary thiaalkylenes having from 4 to 20 carbon atoms.

3. The composition of claim 1 in which the monovalent residues of the monothiols are primary alkyls having from 4 to 20 carbon atoms.

4. The composition of claim 1 in which the divalent residues of the thiadiols are primary thiaalkylenes having from 4 to 20 carbon atoms and the monovalent residues of the monothiols are primary alkyls having from 4 to 20 carbon atoms.

5. The composition of claim 1 in which the monovalent residues of the monothiols are primary aralkyls having from 7 to 20 carbon atoms.

6. The composition of claim 1 in which the divalent residues of thiadiol are oxa-thiaalkylenes having from 4 to 20 carbon atoms.

7. The composition of claim 1 which is the liquid phase reaction product of a primary thiadiol, formaldehyde and a monothiol.

8. The composition of claim 1 in which the thiadiol is thiodiglycol.

9. The composition of claim 1 in which the monothiol is dodecyl mercaptan.

10. The composition of claim 1 in which the monothiol is tridecylmercaptan.

* * * * *